(12) United States Patent
Woolley et al.

(10) Patent No.: US 10,086,187 B2
(45) Date of Patent: Oct. 2, 2018

(54) DRUG DELIVERY APPARATUS

(71) Applicant: RENISHAW (IRELAND) LIMITED, Swords (IE)

(72) Inventors: Maxwell Roy Woolley, Bristol (GB); David Roberts McMurtry, Stancombe (GB); Steven Streatfield Gill, Bristol (GB)

(73) Assignee: RENISHAW (IRELAND) LIMITED, Wotton-under-Edge (GB)

( * ) Notice: Subject to any disclaimer, the term of this patent is extended or adjusted under 35 U.S.C. 154(b) by 876 days.

(21) Appl. No.: 14/374,362

(22) PCT Filed: Feb. 7, 2013

(86) PCT No.: PCT/EP2013/052458
§ 371 (c)(1),
(2) Date: Jul. 24, 2014

(87) PCT Pub. No.: WO2013/117659
PCT Pub. Date: Aug. 15, 2013

(65) Prior Publication Data
US 2014/0371679 A1 Dec. 18, 2014

(30) Foreign Application Priority Data
Feb. 7, 2012 (GB) .................................. 1202091.3

(51) Int. Cl.
*A61M 39/02* (2006.01)
*A61M 39/04* (2006.01)
(Continued)

(52) U.S. Cl.
CPC ..... *A61M 39/0247* (2013.01); *A61B 17/3403* (2013.01); *A61M 39/04* (2013.01);
(Continued)

(58) Field of Classification Search
CPC .............. A61M 39/0247; A61M 39/04; A61M 2039/0081; A61M 2039/0205;
(Continued)

(56) References Cited

U.S. PATENT DOCUMENTS 2,682,268 A  6/1954  Ryan et al.
3,750,645 A  8/1973  Bennett et al.
(Continued)

FOREIGN PATENT DOCUMENTS

CN  2157140 Y  2/1994
CN  1395535 A  2/2003
(Continued)

OTHER PUBLICATIONS

Dec. 2, 2016 Office Action issued in Japanese Patent Application No. 2014-555265.
(Continued)

*Primary Examiner* — Kami A Bosworth
(74) *Attorney, Agent, or Firm* — Oliff PLC

(57) ABSTRACT

Percutaneous access apparatus is described that includes a percutaneous fluid access device having an extracorporeal portion, one or more ports accessible from the extracorporeal portion and a septum for sealing each port. A connector device having one or more hollow needles is attachable to the percutaneous fluid access device. The apparatus also includes an attachment mechanism for attaching the connector device to the extracorporeal portion and an actuation mechanism that, after the connector device has been attached to the extracorporeal portion, can be used to drive the one or more hollow needles through the septum to establish fluid communication between the one or more hollow needles and the one or more ports. The apparatus may be used for neurosurgery applications.

15 Claims, 11 Drawing Sheets

Figure 1:
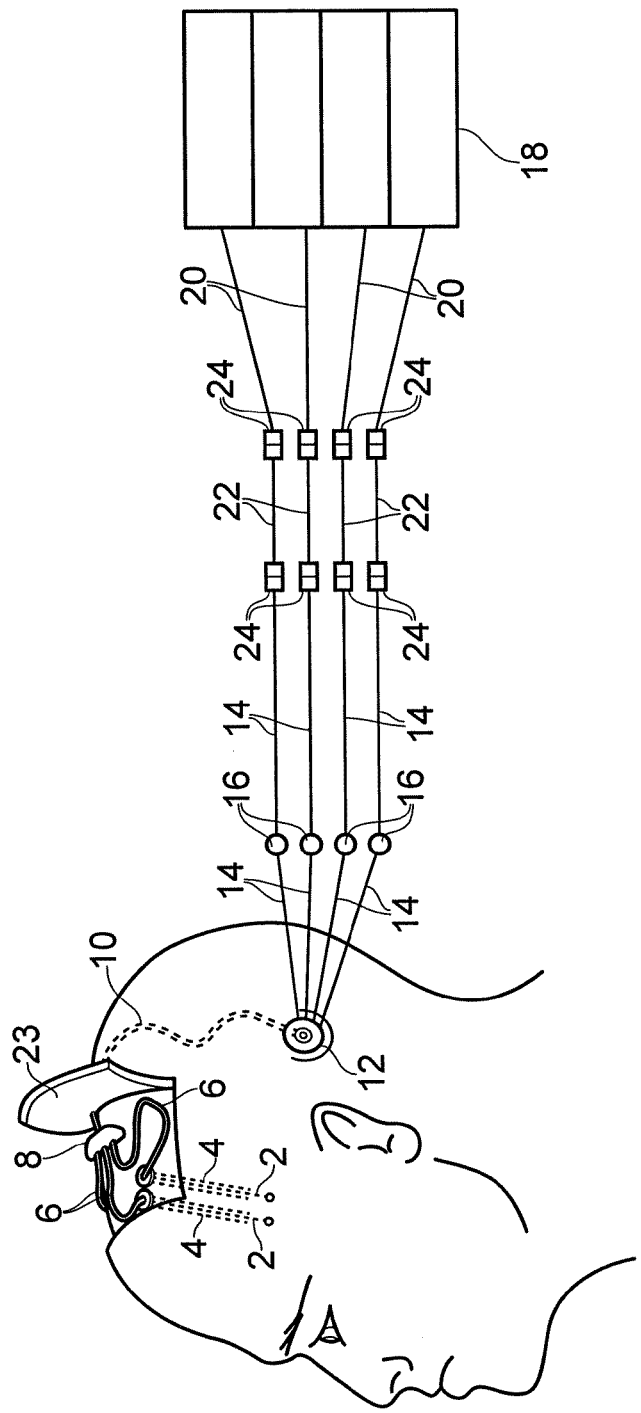

(51) Int. Cl.
*A61M 39/10* (2006.01)
*A61B 17/34* (2006.01)
*A61M 39/00* (2006.01)

(52) U.S. Cl.
CPC ........ *A61M 39/10* (2013.01); *A61M 39/1011* (2013.01); *A61M 39/105* (2013.01); *A61M 2039/009* (2013.01); *A61M 2039/0081* (2013.01); *A61M 2039/0205* (2013.01); *A61M 2039/025* (2013.01); *A61M 2039/027* (2013.01); *A61M 2039/0261* (2013.01); *A61M 2039/0264* (2013.01); *A61M 2039/0276* (2013.01); *A61M 2039/0282* (2013.01); *A61M 2039/0288* (2013.01); *A61M 2039/042* (2013.01); *A61M 2039/1033* (2013.01); *A61M 2039/1044* (2013.01); *A61M 2210/0693* (2013.01)

(58) Field of Classification Search
CPC .... A61M 2039/025; A61M 2039/0261; A61M 2039/0264; A61M 2039/027; A61M 2039/0276; A61M 2039/0282; A61M 2039/0288; A61M 2039/0294; A61M 2039/042; A61M 5/3287; A61M 2005/14252; A61M 2005/14284; A61M 2005/1585
See application file for complete search history.

(56) References Cited

U.S. PATENT DOCUMENTS

| | | | |
|---|---|---|---|
| 4,152,269 A | 5/1979 | Babson | |
| 4,392,851 A | 7/1983 | Elias | |
| 4,578,063 A | 3/1986 | Inman et al. | |
| 4,695,273 A | 9/1987 | Brown | |
| 4,946,445 A | 8/1990 | Lynn | |
| 5,069,671 A | 12/1991 | Theeuwes | |
| 5,088,984 A | 2/1992 | Fields | |
| 5,139,483 A | 8/1992 | Ryan | |
| 5,281,206 A | 1/1994 | Lopez | |
| 5,292,308 A | 3/1994 | Ryan | |
| 5,330,426 A | 7/1994 | Kriesel et al. | |
| 5,368,586 A | 11/1994 | Van Der Heiden et al. | |
| 5,393,101 A | 2/1995 | Matkovich | |
| 5,728,103 A * | 3/1998 | Picha | A61B 17/3423 604/174 |
| 5,932,222 A | 8/1999 | Randolph et al. | |
| 5,954,687 A * | 9/1999 | Baudino | A61M 25/02 604/174 |
| 6,007,516 A | 12/1999 | Burbank et al. | |
| 6,080,132 A | 6/2000 | Cole et al. | |
| 6,302,866 B1 * | 10/2001 | Marggi | A61M 25/0097 604/174 |
| 6,343,717 B1 | 2/2002 | Zhang et al. | |
| 6,609,020 B2 | 8/2003 | Gill | |
| 6,685,674 B2 * | 2/2004 | Douglas | A61M 5/158 604/167.05 |
| 7,329,262 B2 | 2/2008 | Gill | |
| 7,553,290 B1 * | 6/2009 | Asfora | A61B 5/031 604/174 |
| 8,333,769 B2 * | 12/2012 | Browne | A61B 17/1615 606/185 |
| 8,597,237 B2 | 12/2013 | Yow et al. | |
| 2003/0028156 A1 | 2/2003 | Juliar | |
| 2005/0015075 A1 | 1/2005 | Wright et al. | |
| 2005/0113761 A1 | 5/2005 | Faust et al. | |
| 2007/0060879 A1 * | 3/2007 | Weitzner | A61B 17/12045 604/95.04 |
| 2007/0106243 A1 | 5/2007 | Faries et al. | |
| 2007/0262076 A1 | 11/2007 | Johnson | |
| 2008/0100061 A1 | 5/2008 | Sage et al. | |
| 2008/0108950 A1 * | 5/2008 | Rioux | A61B 17/064 604/181 |
| 2008/0197626 A1 | 8/2008 | Coambs et al. | |
| 2008/0243085 A1 | 10/2008 | Destefano | |
| 2009/0082758 A1 | 3/2009 | Gill et al. | |
| 2009/0221971 A1 * | 9/2009 | Mejlhede | A61M 5/142 604/180 |
| 2009/0224529 A1 | 9/2009 | Gill | |
| 2010/0042070 A1 | 2/2010 | Gill et al. | |
| 2011/0054518 A1 | 3/2011 | Carbunaru et al. | |
| 2011/0125104 A1 | 5/2011 | Lynn | |
| 2012/0184939 A1 | 7/2012 | Reiter et al. | |

FOREIGN PATENT DOCUMENTS

| | | |
|---|---|---|
| CN | 2848195 Y | 12/2006 |
| CN | 101384286 A | 3/2009 |
| CN | 101400401 A | 4/2009 |
| CN | 101541356 A | 9/2009 |
| CN | 101754743 A | 6/2010 |
| DE | 10143820 A1 | 3/2003 |
| EP | 0 340 427 A2 | 11/1989 |
| EP | 0 553 534 A1 | 8/1993 |
| EP | 0792661 A2 | 9/1997 |
| EP | 1086804 A2 | 3/2001 |
| FR | 2696526 A1 | 4/1994 |
| GB | 2210268 A | 6/1989 |
| JP | S61-122870 A | 6/1986 |
| JP | 2005-034178 A | 2/2005 |
| JP | 2007-510498 A | 4/2007 |
| JP | 2008-522736 A | 7/2008 |
| JP | 2008-539992 A | 11/2008 |
| JP | 2009-529937 A | 8/2009 |
| JP | 2010-510016 A | 4/2010 |
| WO | WO 02/089725 A2 | 11/2002 |
| WO | WO 02/089900 A1 | 11/2002 |
| WO | WO 2003/077785 A1 | 9/2003 |
| WO | WO 2006/062912 A1 | 6/2006 |
| WO | 2006/122406 A1 | 11/2006 |
| WO | WO 2007/104961 A1 | 9/2007 |
| WO | WO 2008/062173 A1 | 5/2008 |
| WO | WO 2011/098769 A1 | 8/2011 |

OTHER PUBLICATIONS

Nov. 24, 2016 Office Action issued in Japanese Patent Application No. 2014-555266.
Jul. 24, 2014 U.S. Appl. No. 14/374,383 issued by Lewis et al.
Jul. 24, 2014 U.S. Appl. No. 14/374,317 issued by Irving et al.
Aug. 1, 2013 International Search Report issued in PCT/EP2013/052461.
May 9, 2012 British Search Report issued in British Patent Application No. 1202093.9.
Jul. 5, 2013 International Search Report issued in PCT/EP2013/052463.
May 3, 2012 British Search Report issued in British Patent Application No. 1202094.7.
Jul. 8, 2013 International Search Report issued in PCT/EP2013/052458.
May 14, 2012 British Search Report issued in British Patent Application No. 1202091.3.
Aug. 1, 2013 Written Opinion issued in PCT/EP2013/052461.
Jul. 2, 2013 Written Opinion issued in PCT/EP2013/052463.
Jul. 31, 2013 Written Opinion issued in PCT/EP2013/052458.
Nov. 23, 2015 Office Action issued in Chinese Patent Application No. 201380016838.3.
Dec. 2, 2015 Office Action issued in Chinese Patent Application No. 201380017547.6.
Nov. 18, 2016 Office Action issued in Japanese Patent Application No. 2014-555264.
Sep. 22, 2015 Office Action issued in Chinese Patent Application No. 201380017581.3.
Dec. 2, 2015 Office Action issued in U.S. Appl. No. 14/374,317.
Aug. 28, 2017 Office Action issued in U.S. Appl. No. 14/374,383.
Nov. 1, 2017 Office Action issued in Japanese Patent Application No. 2014-555265.

(56) References Cited

OTHER PUBLICATIONS

Fumihide Miyashita, "Precise Measurement of Mass and Volume," The Japan Society for Analytical Chemistry, 2008, pp. 2-10.
Sep. 20, 2017 Office Action issued in Japanese Patent Application No. 2014-555264.
Apr. 23, 2018 Office Action issued in U.S. Appl. No. 14/374,383.

* cited by examiner

SECTION A-A

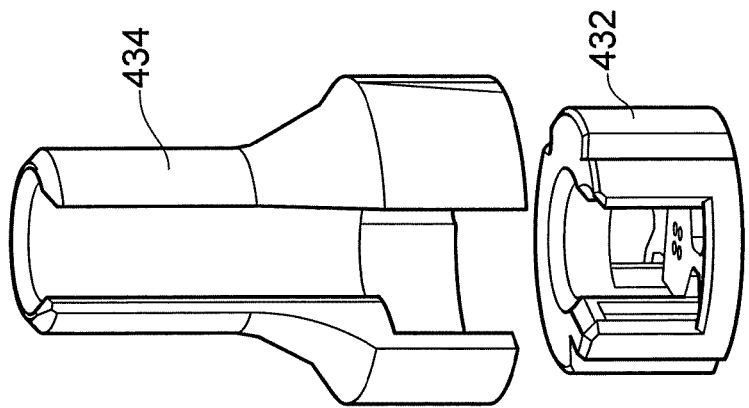
FIG. 13A
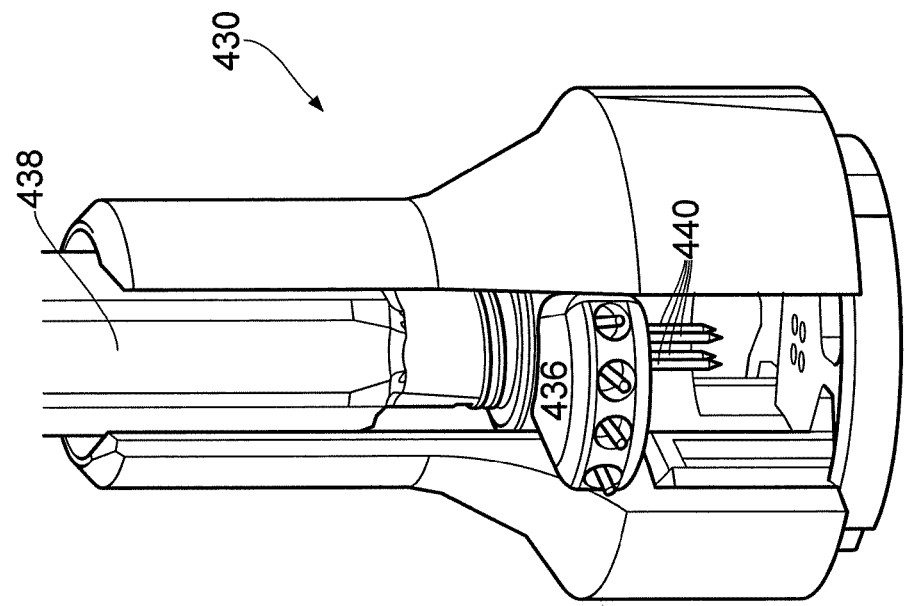
FIG. 13B
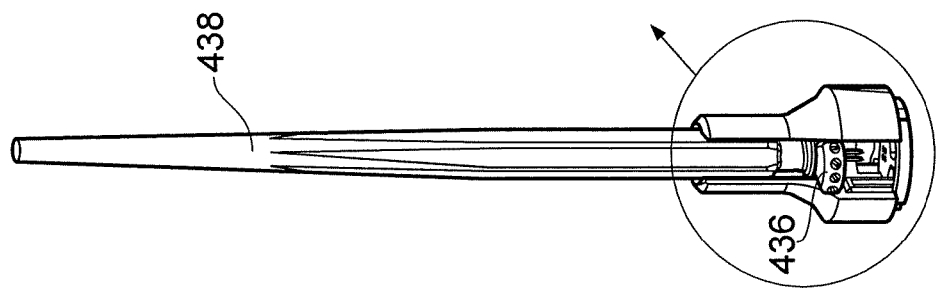

DRUG DELIVERY APPARATUS

The present invention relates to medical apparatus and in particular to the various components of an apparatus for delivering fluids, such as drugs, to different parts of the human or animal body. In one aspect, the present invention relates to a percutaneous access apparatus that may form part of a drug delivery apparatus for delivering therapeutic agent to the brain.

The drug treatment of a number of neuro-degenerative disorders, hereditary neurological disorders, brain tumours and other diseases of the nervous system are compromised by the presence of the blood brain barrier which prevents the transfer of drugs from the vascular system or cerebrospinal fluid into the brain substance. Examples of drugs which do not adequately cross the blood brain barrier include protein molecules such as neurotrophins, monoclonal antibodies, viral particles for delivery of gene therapy, as well as a number of cytotoxic drugs for the treatment of tumours. It has been described previously how such drugs can be delivered to the brain by direct infusion into the parenchyma via one or more indwelling catheter. For example, a guide tube and catheter system is described in U.S. Pat. No. 6,609,020. A catheter with a small external diameter that can be precisely positioned in the brain is described in WO2003/077785. Percutaneous access ports have also been described in WO2008/062173 and WO2011/098769.

According to a first aspect of the present invention, there is provided percutaneous access apparatus, comprising a percutaneous fluid access device comprising an extracorporeal portion, one or more ports accessible from the extracorporeal portion and a septum for sealing each port, and a connector device comprising one or more hollow needles, wherein the apparatus includes an attachment mechanism for attaching the connector device to the extracorporeal portion and an actuation mechanism that, after the connector device has been attached to the extracorporeal portion, can be used to drive the one or more hollow needles through the septum to establish fluid communication between the one or more hollow needles and the one or more ports.

The first aspect of the present invention thus relates to percutaneous access apparatus. The apparatus comprises two main components. Firstly, there is the percutaneous fluid access device that may be implanted within the subject. The percutaneous fluid access device comprises an extracorporeal portion (i.e. a part of the device that is located outside of, and protrudes from, the body), one or more ports that are accessible from the extracorporeal portion and a septum for sealing each port. Secondly, a connector device is provided that comprises one or more hollow needles. The connector device, which remains outside of the body, can be connected to external fluid pumps or the like and can also be connected to the percutaneous fluid access device whenever fluid access is required.

The percutaneous access apparatus includes an attachment mechanism for attaching (i.e. securing) the connector device to the extracorporeal portion. As explained in more detail below, this attachment mechanism preferably allows the connector device and extracorporeal portion to be locked or placed together in a precise and repeatable relative position. An actuation mechanism is also provided that, after the connector device has been attached to the extracorporeal portion, can be used to drive the one or more hollow needles through the septum to establish fluid communication between the one or more hollow needles and the one or more ports. The actuation mechanism, which is also described in more detail below, is preferably manually activated by rotation of a knurled hub or the like.

The present invention thus establishes fluid communication between the connector device and extracorporeal portion of the percutaneous fluid access device in two stages. The connector device is firstly attached to the extracorporeal portion of the percutaneous fluid delivery device (i.e. secured or fixed to the extracorporeal portion without a fluidic link being established). After attachment, the actuation mechanism can be used to drive the tips of the hollow needles through the septum and thus establish a fluidic link with the associated ports. This arrangement has the advantage that correct alignment of the connector device with the ports of the percutaneous fluid access device is provided before the hollow needles engage the septum. Preferably, the hollow needles are aligned with an accuracy better than 0.2 mm, more preferably better than 0.1 mm and even more preferably better than 0.05 mm. This reduces the risk of the hollow needles being damaged (e.g. bent) or damaging the septum during attachment/removal. Furthermore, the hollow needles pierce the septum in the same place each time the fluid connection is established thereby increasing the lifetime of the septum. The present invention, in one embodiment, can also protect the clinician from a sharps risk by only extending the hollow needles after engagement of the connector device with the extracorporeal portion. A more robust and reliable percutaneous access apparatus is thereby provided.

The percutaneous access apparatus of the present invention has a variety of different applications. It can, for example, be used to deliver fluid to one or more locations within the brain parenchyma via suitably implanted catheters. Delivery of therapeutics, contrast agents and other fluids can be achieved intermittently through re-accessing the percutaneous fluid access device, which is conveniently situated in/on the skull of the subject. The apparatus could, for example, be used to deliver drugs for indications such as Parkinson's disease, Alzheimer's, oncology and other neurological diseases. The drug can be used for chronic, subchronic and acute delivery of therapeutics to the patient. It should also be noted that the apparatus is not only suitable for human use but could also be used for animals.

Advantageously, the attachment mechanism includes a first set of features on the extracorporeal portion. A second set of features are preferably provided on the connector device. The first and second sets of features conveniently provide, when engaged, accurate alignment of the connector device with the extracorporeal portion. In a preferred embodiment, the attachment mechanism provides a kinematic or pseudo-kinematic connection between the extracorporeal portion and the connector device. Providing such a kinematic or pseudo-kinematic connection, in which each of the six degrees of freedom of motion between the two bodies is constrained by a single point of contact, ensures accurate and repeatable alignment of the extracorporeal portion and the connector device. For example, the first set of features may include a vertical groove, a horizontal groove and a conical recess. The second set of features may include three spaced apart balls. Engagement of the balls with the grooves and recess can provide such high accuracy, kinematic, alignment. One or more macro-alignment features may also be provided to ensure correct general or macro alignment of the first and second sets of features. The ability to provide repeatable alignment between the extracorporeal portion and the connector device is advantageous because it means that the correct alignment of the one or more hollow needles with the one or more ports can be ensured.

After the actuation mechanism has been used to drive the one or more hollow needles of the connector device into the one or more ports, at least part of the attachment mechanism and/or at least part of the actuation mechanism may be detached. For example, the attachment mechanism may comprise a protruding guide element along which the connector device is driven by the actuation mechanism. After the fluid connection has been established, this guide element may be detached. This allows, for example, a longer guide element to be used whilst establishing the fluid link (e.g. to make establishment of such a fluidic link easier for medical personnel) but for such a guide element to be removed during fluid infusion (e.g. for patient comfort/convenience). Similarly, the actuation mechanism may include a mechanism for driving the connector device toward the port(s) of the percutaneous fluid access device that can be detached after the necessary fluidic link has been established.

The apparatus may comprise one hollow needle and one port; i.e. single channel percutaneous access apparatus may be provided. Advantageously, the apparatus comprises a plurality of hollow needles and a plurality of ports. Preferably, the same number of hollow needles and ports are provided. In this manner, a plurality of separate fluid pathways may be provided through the percutaneous access apparatus. For example, the percutaneous access apparatus may provide at least two, at least three, at least four or at least five separate fluid pathways (e.g. it may comprise at least two, at least three, at least four or at least five hollow needles and ports). In a preferred embodiment, four separate fluid pathways (e.g. four needles and four ports) are provided.

If multiple ports and hollow needles are provided, the attachment mechanism preferably allows repeatable, preferably unique, alignment of each hollow needle with a predetermined one of the ports. In other words, it is preferred that the extracorporeal portion and the connector device can only be connected together in a single relative orientation. This ensures that the same hollow needle always enters the same port and hence reduces the risk of incorrect fluid connections being established. This is particularly important if different volumes, or different therapeutic agents, are to be delivered to different target sites.

Conveniently, the attachment mechanism comprises a locking device for releasably locking the connector device to the extracorporeal portion. In other words, the connector device may be securely locked to the extracorporeal portion (e.g. during fluid delivery). The extracorporeal portion may comprise the locking device. Advantageously, the connector device comprises the locking device. Providing the locking device as part of the connector device allows the profile and size of the extracorporeal portion to be minimised.

The skilled person would appreciate the numerous ways to implement a compact and reliable locking device. Advantageously, the locking device comprises a screw and a hinged engagement member. Tightening the screw may be used to deflect the hinged engagement member into contact with the extracorporeal portion thereby locking the connector device to the extracorporeal portion. Preferably, the hinge acts as a spring so that releasing the screw causes disengagement (i.e. it unlocks the connector device from the extracorporeal portion).

The attachment mechanism preferably includes an indicator to indicate that the connector device has been securely attached to the extracorporeal portion of the percutaneous fluid access device. This indicator ensures that the user knows when the connector device has been properly attached and hence that it is possible to use the actuation mechanism to drive the needles into the septa. The indicator may be an indicator of any type. For example, it may be a sensory indicator such as a visual or tactile indicator.

Advantageously, the connector device comprises a needle holder for holding the one or more hollow needles. Each hollow needle may comprise an aperture at its tip. Preferably, each needle comprises a (solid) sharp tip and an aperture in its side wall. The needle holder is preferably movable relative to the rest of the connector device (e.g. it can be moved within the housing or body of the connector device). When the connector device is attached to the extracorporeal portion, the needle holder is preferably moveable relative to the extracorporeal portion. This allows the hollow needles to be moved into engagement with the ports.

The needle holder may be located in, and more preferably is retained within, an axial alignment channel defined by (e.g. formed within) the connector device. Preferably, the longitudinal axis of the axial alignment channel is, when the connector device is attached to the percutaneous fluid access device, substantially perpendicular to the septum. Advantageously, the needle holder can be translated back and forth along the axial alignment channel. In such an arrangement, the longitudinal axes of the one or more hollow needles of the needle holder are preferably aligned with the axis of the alignment channel. In this manner, translation of the needle holder along the alignment channel towards the extracorporeal surface can drive the one or more needles through the septum into the one or more ports.

The actuation mechanism may be used to drive the needle holder back and forth along the alignment channel. The actuation mechanism may comprise an elongate shaft with the needle holder attached to its distal end. The elongate shaft may then be used to push the needle holder along the alignment channel until the hollow needles pierce the septum and enter the ports. A stop may be provided in the connector device to set the depth of needle penetration into the ports. In a preferred embodiment, the needle holder is attached to the distal end of a threaded shaft. The threaded shaft is also preferably retained in the threaded channel through a rotatable knurled hub. Preferably, rotation of the knurled hub causes translation of the threaded shaft and hence moves the needle holder back and forth along the alignment channel. Advantageously, the connector device also comprises a retaining hub or connector base. The retaining hub may be held stationary (e.g. using one hand) whilst the knurled hub is rotated (e.g. using the other hand) thereby preventing significant torque being applied to the interface between the bone and the percutaneous fluid access device. The hollow needles are thus brought into engagement with the septum from a direction substantially normal to the septum surface thereby minimising the risk of damage to components of the apparatus. Although manually operated actuation mechanisms are described above, it should be noted that automated (e.g. electrical) actuation mechanisms could be alternatively be provided.

The percutaneous fluid access device preferably comprises a subcutaneous base portion. The subcutaneous base portion is, when implanted, preferably located below the outer surface of the skin. The one or more ports preferably extend through the subcutaneous base portion. Advantageously, the subcutaneous base portion comprises one or more port outlets. Each of these one or more port outlets may be connected, or connectable, to one or more implanted catheters. The port outlets may comprise multiple single lumen tubes or a multi-lumen tube. The fluid pathways (e.g. tubes) may exit the device at between 70-110 degrees to the longitudinal axis of the device (e.g. from an approximately perpendicular direction). The tubes thus preferably exit the device from the side and not from beneath the device; the tube can thus exit the device in the bone level.

Advantageously, the channels through the percutaneous fluid access device have a low dead volume. This maximises the therapeutic delivery during re-accesses as inert fluid rests in the system between infusions. Preferably, the dead volume of each channel is less than 500 microlitres, more preferably less than 250 microlitres, more preferably less than 100 microlitres and more preferably less than 50 microlitres.

The percutaneous fluid access device preferably comprises a subcutaneous base portion that is at least partially insertable into a complementary recess formed in a bone. The percutaneous fluid access device is thus preferably a bone anchored percutaneous fluid access device. Preferably, the percutaneous fluid access device is not a skin anchored device. Advantageously, the subcutaneous base portion also comprises one or more features (e.g. annular circumferential features such as ribs) for gripping the internal surface of such a complementary recess thereby directly anchoring the subcutaneous base portion to the bone. The percutaneous fluid access device may thus be retained in bone through an interference or press fit; this maximises retention of the subcutaneous base portion after implantation.

The subcutaneous base portion may comprise a rough surface to encourage rapid osseointegration. Similarly, the percutaneous portion of the device (i.e. the part in contact with the skin) may comprise a roughened region to promote dermal integration (e.g. the tissue around the percutaneous portion of the device will heal to the device and/or to the periosteal layer thereby providing a healed seal around the device to minimise infection and/or rejection). Although not essential, additional coatings such as Hydroxyappetite could be used to provide a roughened coating to accelerate and strengthen dermal attachment and/or osseointegration. The percutaneous portion may also include a smooth (e.g. polished or coated) region located above the roughened region to which the skin adheres. The smooth portion inhibits tissue in-growth and can be kept clean, thereby reducing the risk of infection of the underlying dermis. Preferably, the percutaneous fluid access device is arranged to be anchored to a recess formed in the skull. Further details of a bone anchored percutaneous fluid access device are described in WO2011/098769.

The percutaneous fluid access device may be formed using a variety of manufacturing techniques. The device could also be manufactured from a range of different materials. For example, the device could be formed from a ceramic (e.g. Zirconia) and/or PEEK if use in MRI sensitive environments is required. Advantageously, manufacture of the percutaneous fluid access device comprises using a selective melting (e.g. selective laser melting) technique in which components of the device are formed by selectively melting powdered material (e.g. powdered metal). Such techniques are also termed rapid manufacturing or printing. The device may thus comprise printed or cast titanium. In a preferred embodiment, a flared tube is provided within the main body of the device; this tubing is retained during injection moulding. Advantageously, the percutaneous fluid access device is implanted after it has been fully assembled. In other words, all the constituent parts of the percutaneous fluid access device are preferably combined prior to implantation.

The percutaneous fluid access device may comprise a plurality of ports and separate septa may be provided for the different ports. Advantageously, the percutaneous fluid access device comprises a plurality of ports and a single septum is provided to cover each of the plurality of port. Preferably, the single septum can be accessed and removed via the extracorporeal portion of the percutaneous fluid access device. Conveniently, the septum is compressed and retained using a press fit, an interference fit or a snap fit cap. A filter unit may also be provided as part of percutaneous access apparatus; e.g. a filter could be provided underneath the septum allowing it to be replaced if the septum was removed.

The invention also extends to a kit comprising the percutaneous access apparatus and at least one implantable catheter device. The kit may also include a guide tube. The kit may also include at least one bacterial and/or air filter. The percutaneous access apparatus may be used for any medical purpose. Preferably, the percutaneous access apparatus is used for neurosurgical purposes. Although the apparatus is mainly described for delivering fluid, it should be noted that the apparatus is also suitable for collecting (aspirating) fluid from the body. The cross-sectional area of the fluid channel through each component of the kit may be substantially the same.

According to a further aspect of the invention, there is provided a connector device for attachment to a percutaneous fluid access device, comprising; one or more hollow needles, an attachment mechanism for attaching the connector device to the extracorporeal portion of an associated percutaneous fluid access device, and an actuation mechanism for driving the one or more hollow needles towards an attached percutaneous fluid access device. The attachment mechanism and/or the actuation mechanism may be fully integrated within the connector device. At least part of the attachment mechanism may be removable from the connector device. At least part of the actuation mechanism may be removable from the connector device. In this manner, some or all of the attachment mechanism and/or the actuation mechanism may be detached from the connector device after the required fluidic connection(s) with the percutaneous fluid access device has been established.

The actuation mechanism of the connector device thus allows, after the connector device has been secured to the extracorporeal portion, the hollow needles to be driven through the septum of the attached percutaneous fluid access device to establish fluid communication with the ports of the percutaneous fluid access device. The connector device may include any of the features described above.

According to a further aspect of the invention, there is provided a connector device attachable to a port via a kinematic or pseudo-kinematic interface. The kinematic or pseudo-kinematic interface ensures accurate alignment of the connector device and the port. The port may be a percutaneous port (e.g. a percutaneous fluid access device as described above).

According to a further aspect of the present invention, a guide device is provided for attachment to a percutaneous fluid access device. The guide device may be directly or indirectly attachable to the percutaneous fluid access device. The guide device may, for example, be directly or indirectly attached to the extracorporeal surface of a percutaneous fluid access device as described herein. If directly attached, the guide device may include features for engaging corresponding features of the extracorporeal surface of the percutaneous fluid access device. The guide device may thus be directly attachable to the extracorporeal surface via a kinematic or pseudo-kinematic interface as described above. If indirectly attached, the guide device may be attached (optionally via a kinematic or pseudo-kinematic interface) to one or more components that are in turn attached (optionally via a kinematic or pseudo-kinematic interface) to the extracorporeal surface of the percutaneous fluid access device.

The guide device is preferably arranged to guide a connector device into engagement with the percutaneous fluid access device. The connector device may comprise one or more hollow needles, as described above. The percutaneous fluid access device may comprise one or more ports for receiving such needles, as also described above. The guide device may thus act to guide the connector device as it is brought into engagement with the percutaneous fluid access device. In particular, the guide device preferably guides the one or more hollow needles of the connector device into engagement with the one or more ports of the percutaneous fluid access device. It should be noted that such a guide device may be used with an actuation mechanism as described elsewhere herein or the connector device may simply be pushed by hand into engagement with the percutaneous fluid access device to establish the fluidic link(s) (optionally using a rod or other element that can be attached to the connector device). Preferably, the guide device can be detached after the fluidic connection is established between the connector device and the percutaneous fluid access device. The guide device may thus be used during connector device attachment but removed before any subsequent infusions. The guide device may include an elongate protruding channel along which the connector device can be passed. The guide device may protrude further from the percutaneous fluid access device than the connector device. For example, the guide device may be at least 3 cm, at least 5 cm or at least 10 cm long.

According to a further aspect of the present invention, there is provided a percutaneous fluid access device comprising an extracorporeal portion, one or more ports accessible from the extracorporeal portion and a septum for sealing each port. The extracorporeal portion may comprise a kinematic or pseudo-kinematic interface for an associated connector device. Advantageously, the percutaneous fluid access device comprises a subcutaneous portion (the portion underneath the skin that can include the part anchored to the bone recess) and a percutaneous portion (i.e. a part that passes through the skin). Conveniently, the percutaneous fluid access device includes an increase in cross-sectional from the subcutaneous portion. In other words, the percutaneous fluid access device preferably increases in cross-sectional area (e.g. diameter) with distance from the skin surface. The percutaneous portion may thus be tapered. For example, it may comprise a tapered cone. Preferably, the angle of the taper (from the skin surface normal) is greater than 5°, or greater than 10°, or greater than 15°. Preferably, the angle of the taper is less than 40°, or less than 35°, or less than 30° or less than 25°. Such an outwardly tapered profile stops tissue overgrowth of the device after implantation.

The invention also extends to a method of neurosurgery, the method comprising the step of implanting at least part of the above percutaneous access apparatus. Catheter, tubing and other components may also be implanted. The implanted apparatus may be used to deliver therapeutic agent to the central nervous system.

According to a further aspect of the invention, fluid storage apparatus for medical use is provided, the apparatus comprising a length of tubing having a first end and a second end, a first sealable connector portion being provided at the first end and a second sealable connector portion being provided at the second end, wherein the volume of fluid that can be stored within the apparatus is known.

Fluid storage apparatus is thus provided that allows a precise volume of fluid (e.g. a fluid or infusate optionally comprising a therapeutic agent) to be stored. In use, the therapeutic agent is loaded into the tubing and the ends of the tubing are sealed. A quantity of fluid can thus be stored in the apparatus that is equal to the internal volume of the fluid storage apparatus; the internal volume being the internal volume of the tubing plus any internal volume of the first and second connector portions.

The fluid storage apparatus has a number of advantages. For example the volume of fluid contained with the storage apparatus can be defined with a greater resolution than a typical syringe thereby providing improved control over the amount of fluid delivered to a subject. Furthermore, the fluid storage apparatus can be readily inserted in the fluid line between a fluid pump and a catheter implanted in the patient. A precise amount of fluid can be delivered and almost no residual fluid will remain in the delivery system; i.e. there is no substantial fluid mixing and all the stored fluid is pushed from the fluid storage apparatus to the catheter for delivery to the target site. Although the fluid storage apparatus is highly suited to neurological applications where small and precisely known quantities of therapeutic agent are delivered, it should be recognised that the apparatus is suitable for any medical application.

The fluid storage apparatus has a number of advantages. For example, it may be loaded by a pharmacist in a clean environment thereby reducing the chance of an error being made on the ward. There is also no need to provide Y-connectors as part of the drug delivery system (Y-connectors typically having a large dead volume) and also a reduced chance of bubbles entering the system. The fluid storage apparatus also allows for the safe storage and transport of drug; this is especially advantageous when using cytotoxic (chemotherapy) drugs or the like.

As mentioned above, the volume of fluid that can be stored within the apparatus is known. This knowledge may arise from measuring the internal volume of the apparatus or by theoretically predicting the volume (e.g. from design data). Preferably, the internal volume of the apparatus is known with an accuracy of better than 10%, more preferably better than 5% and even more preferably better than 1%. In a preferred embodiment, the internal volume of the apparatus is known with an accuracy of between 2% and 3%.

Advantageously, the cross-section area of the fluid pathway through the fluid storage apparatus (including the first and second sealable connector portions) is substantially constant. It is also preferred that the cross-section area is small. For example, it is preferred that the cross-sectional area has a internal diameter less than 1 mm, more preferably less than 0.9 mm and more preferably less than 0.8 mm. In a preferred embodiment, an internal diameter of 0.7 mm is provided. The provision of a small, optionally substantially constant, cross-sectional area through the apparatus reduces fluid mixing and the chance of pockets of fluid being bypassed. A line of fluid can thus be pushed down connected tubing towards a catheter.

The first and second sealable connector portions may be provided by any suitable connector portion. For example, stop-cocks or needleless septa may be provided. Preferably, the first and second sealable connector portions have a low dead volume (e.g. a dead volume of less than 50 µl); i.e.

there is only a very small volume in which fluid mixing can occur. Advantageously, one or both of the first and second sealable connector portions comprise a self-sealing connector portion. In other words, the sealable connector portions preferably remain sealed when they are not connected to a complementary connector portion. Preferably, the first and second connector portions are both of the same design.

In a preferred embodiment, each self-sealing connector portion includes a septum. The septum seals the lumen of the length of tubing, thereby ensuring stored fluid is retained therein. Each self-sealing connector portion may also include a twist-lock member. Such a twist lock member is preferably arranged to engage a complementary twist lock member, thereby enabling connection with an associated connector portion by a twist lock action. A complementary fluid connector portion may also be provided (e.g. affixed to the end of associated tubing) that comprising a complementary twist lock member and a lumen, a hollow needle being retained in and protruding from the aperture at the end of the lumen. Engaging the self-sealing connector portion with the complementary fluid connector portion using a twist lock action thus causes the hollow needle of the complementary fluid connector portion to pierce the septum of the self-sealing fluid connector portion thereby establishing a fluid link. The self-sealing connector portion and the complementary fluid connector portion may include internal cylindrical tubes that are dimensioned to slide within one another when the twist lock connection is being established. The internal cylindrical tubes may thus provide relative alignment of the self-sealing connector portion and the complementary fluid connector prior to the needle piercing the septum. This ensures the needle penetrates the septum from the required direction (e.g. perpendicular to the surface normal) and that the septum is pierced in the same location each time a connection is made. Such connectors may, for example, be provided as a modified Luer connector. Further details of such connectors are outlined below.

A complementary fluid connector portion may also be provided that is unattached to a tube or is attached to an open ended tube. This may be used to open or vent the first sealable connector portion whilst the apparatus is being filled with fluid via a complementary connector portion that is attached to the second sealable connector portion. A filling tube (e.g. attached to a syringe or pump) may also be provided that comprises a complementary fluid connector portion at its distal end. The filling tube may then be connected to the second sealable connector portion to enable the apparatus to be filled with fluid.

Advantageously, the internal volume of the apparatus is selected to equal to the volume of therapeutic agent to be delivered to a patient. The apparatus may thus be fabricated to have a certain internal volume that equals a volume of therapeutic agent to be delivered. Alternatively, the apparatus may be made to have a certain internal volume and the required dosage of therapeutic agent may be provided in a volume of fluid that matches the internal volume of the apparatus.

Conveniently, the apparatus comprises a marking and/or label that indicates the internal volume of the apparatus. For example, a label could be affixed to the apparatus, and/or a marking could be applied to the apparatus and/or a part of the apparatus (e.g. the connector portions) could be colour coded to indicate the internal volume.

Advantageously, a therapeutic agent is contained within the length of tubing. In other words, the invention extends to the apparatus in combination with the therapeutic agent stored therein. The volume of therapeutic agent stored in the apparatus is then known. The therapeutic agent may be suitable for delivery the central nervous system. In particular, the therapeutic agent may be for direct infusion into the brain via an intracranial catheter. The therapeutic agent may comprise a protein or virus; such agents can be easily damaged under high pressure (e.g. as found in a syringe) and hence the present apparatus can protect such therapeutic agents from accidental damage. The therapeutic agent may comprise a neurotrophic factor, such as GDNF.

The length of tubing may be of any type. The tubing may comprise fused silica or FEP. Preferably, the length of tubing comprises plastic. The plastic may be flexible. It is preferred that the tubing is of a medical grade. Advantageously, the tubing and is long-term compatible with the therapeutic agent being stored.

According to a further aspect of the invention, fluid delivery apparatus is provided that includes fluid storage apparatus as described above. The fluid delivery apparatus may also comprise an implantable catheter. The fluid delivery apparatus may also comprise an outlet tube from a fluid delivery device (such as a syringe pump). Advantageously, the outlet tube of the fluid delivery device is connectable to the implantable catheter via the fluid storage apparatus. In other words, the fluid storage apparatus can be inserted in the fluid pathway between the outlet tube of the pump and the implantable catheter. There may be a direct connection between the fluid storage apparatus and the catheter and/or the outlet tube. Alternatively, the fluid delivery apparatus may also include additional intermediate components (such as percutaneous access apparatus, hubs, additional supply tubing, filters etc) in the fluid pathway.

In use, the fluid (e.g. therapeutic agent) stored by the fluid storage apparatus is pushed or flushed from the fluid storage apparatus by the flow of fluid from the pump to the catheter. The arrangement provides in-line delivery of the therapeutic agent with minimal fluid mixing. The fluid dispensed by the pump can also be an inert or buffer fluid (e.g. saline or artificial CSF) meaning that the pump does not contain the therapeutic agent and can thus be reused to deliver a different therapeutic agent without having to be flushed clean. There is also no need to have two pumps per delivery line (e.g. one for buffer and one for the therapeutic agent).

The various tubes of the fluid delivery apparatus may all be linked by low dead volume fluid connectors, for example of the type described in more detail below. Preferably, the cross-sectional area (e.g. the diameter) of the fluid pathway from the pump to the catheter tip is substantially constant.

The present invention also extends to a fluid storage kit that comprises a plurality of fluid storage apparatus of the type described above. In particular, the plurality of fluid storage apparatus preferably includes fluid storage apparatus for storing different known volumes of fluid. In other words, a kit containing a plurality of fluid storage apparatus having different storage volumes can be provided. The fluid storage apparatus of most appropriate volume may then be selected (e.g. by a pharmacist) to store a prescribed volume of therapeutic agent.

According to a further aspect of the invention, a fluid storage vessel is provided that comprises a length of tubing containing a defined dosage of therapeutic agent, the length of tubing being sealed at each end. The seal may be provided by a connector portion.

According to a further aspect of the invention, a fluid storage vessel is provided that comprises a length of tubing containing a defined volume of liquid comprising a therapeutic agent, the length of tubing being sealed at each end. The seal may be provided by a connector portion.

According to a further aspect of the invention, there is provided a method for storing a preset volume of fluid comprising a required dosage of therapeutic agent, the method comprising the steps of selecting a length of tubing having a volume equal to the preset volume of fluid, loading the fluid into the length of tubing and sealing each end of the length of tubing. The step of sealing each end of the length of tubing may comprise providing or using fluid connector portions at each end of the length of tubing to seal the tube. Such fluid connector portions may advantageously comprise septum seals. The step of selecting a length of tubing having a volume equal to the preset volume of fluid may comprise selecting an appropriate length of tubing from a kit containing lengths of tubing of different lengths. The step of selecting a length of tubing having a volume equal to the preset volume of fluid may alternatively comprise cutting a length of tubing to the required length.

According to a further aspect of the invention, there is provided a method for dispensing a predetermined dosage of therapeutic agent to a subject. The method comprises the step of connecting a fluid dispensing pump to an implanted catheter via one or more fluid delivery tubes, wherein the method further comprises the step of locating a storage tube in the fluid path from the pump to the catheter, the storage tube containing a known volume of therapeutic agent for delivery to the subject.

According to a further aspect of the invention, there is provided a first fluid connector portion comprising a first twist lock member and a lumen, wherein a septum is provided for sealing the lumen. The lumen may be in fluid communication with an attached tube. The provision of the septum means the first fluid connector portion is self-sealing (i.e. it provides a fluid seal when not connected to a complementary connector portion). This makes it particularly suitable for inclusion in fluid storage apparatus of the type described above.

According to a further aspect of the invention, there is provided a second fluid connector portion comprising a second twist lock member and a lumen, wherein a hollow needle is retained in and protrudes from the aperture at the end of the lumen. The lumen may be in fluid communication with an attached tube. Preferably, the needle has a sharp (pointed) tip. Preferably the needle comprises an aperture in its side wall that is in fluid communication with the lumen of the needle. Providing a side aperture prevents coring during septum penetration. Preferably, the aperture is adjacent the tip. The lumen of the hollow needle may have an outer diameter substantially equal to the internal diameter of the lumen. The lumen of the second fluid connector portion may have an internal diameter substantially equal to the internal diameter of an attached tube. The lumen of the second fluid connector portion may have a diameter of less than 1 mm, more preferably less than 0.9 mm and more preferably less than 0.8 mm. The needle may have an outer diameter of less than 1 mm, more preferably less than 0.8 mm and more preferably less than 0.6 mm. In a preferred embodiment, the needle may have an outer diameter of 0.5 mm and the lumen of the second fluid connector portion (and optionally the first fluid connector portion) may have an internal diameter of 0.7 mm.

The second fluid connector portion is preferably arranged to connect to the first fluid connection portion described above. The lumen of the second fluid connector portion may have the same internal diameter as the lumen of the first fluid connector portion.

The first fluid connector portion may comprise a first internal cylindrical tube co-axial with the lumen thereof. The second fluid connector portion may comprise a second internal cylindrical tube co-axial with the lumen thereof. The first and second internal cylindrical tubes may have different dimensions so that one tube can slide into the lumen of the other tube. For example, the first internal cylindrical tube may be dimensioned to fit within the lumen of the second internal cylindrical tube. The first and second internal cylindrical tubes may be arranged to slide into engagement with one another when the twist lock connection is being established. The first and second internal cylindrical tubes may thus provide relative alignment of the first and second fluid connector portions during twist-lock attachment. This can provide alignment of the needle and the septum. In particular, this arrangement ensures that the needle penetrates the septum from the required direction (e.g. perpendicular to the surface normal) and that the septum is pierced in the same location each time a fluid connection is made. The first and second internal cylindrical tubes can also provide control over how far the hollow needle penetrates the septum. If the hollow needle comprises a fluid aperture in its sidewall, the depth of insertion can be set so that, during attachment, the part of the needle comprising the fluid aperture passes through the septum and the aperture is located adjacent the septum. In this way, the dead volume of the system is minimised.

The present invention also extends to a fluid connector that comprises a first fluid connector portion and a second fluid connector portion as described above. The first and second twist lock members of the first and second fluid connector portions are preferably arranged to co-operate to provide a twist lock connection between the first and second fluid connector portions. The first twist lock member may comprise a male Luer lock arrangement. The second twist lock member may comprise a female Luer lock arrangement. Engaging the first fluid connector portion and the second fluid connector portion using a twist lock action preferably causes the hollow needle of the second fluid connector portion to pierce the septum of the first fluid connector portion. A fluid link between the lumens of the first and second connector portions (and hence between two lengths of tubing) can thus be established. It should also be noted that the second fluid connector portion can also establish a fluid link with a connector portion that does not include a septum.

Connectors of the above described type are particularly advantageous because they have a low dead volume. This means they are especially suited to neurological applications where relatively small amounts of fluid (e.g. hundreds of microlitres) are dispensed.

The present invention also extends to apparatus for delivery of fluid to the brain via one or more intracranial catheters, the apparatus also comprising one or more the following; a percutaneous access apparatus, a connector device, a fluid storage apparatus, a fluid delivery apparatus; and fluid connectors. External drug deliver pumps (e.g. syringe pumps) may also be provided. Advantageously, the apparatus has a low dead volume.

Figure 2A:
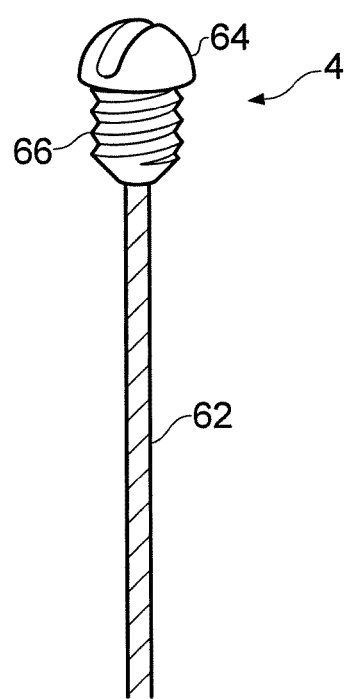
Figure 2B:
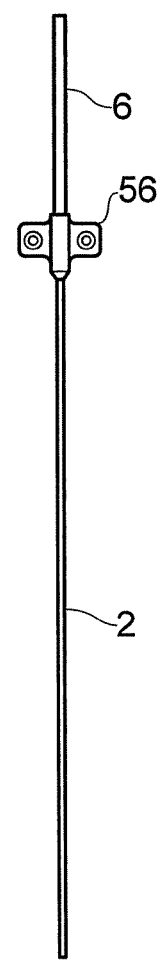
Figure 3A:
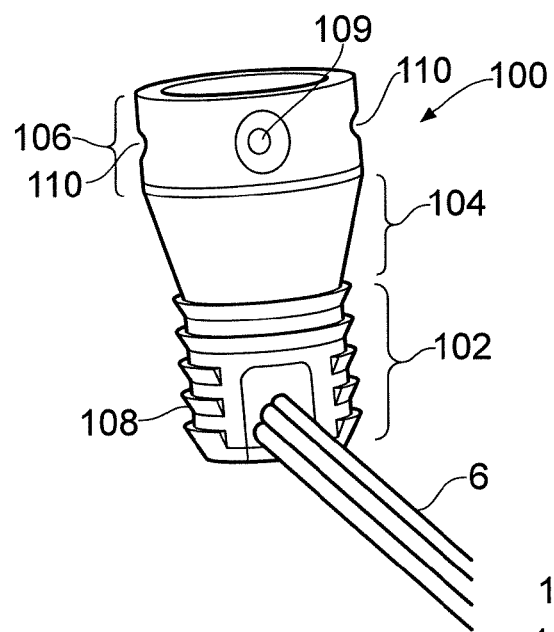
Figure 3B:
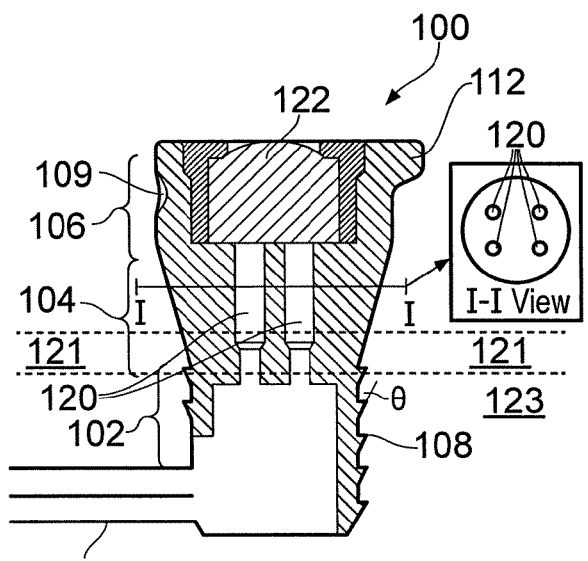
Figure 3C:
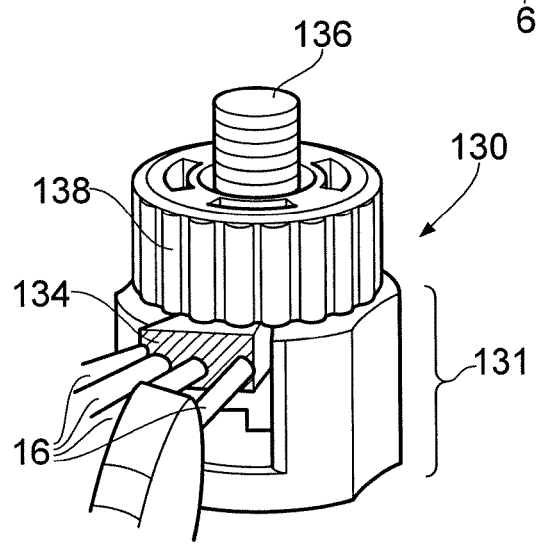
Figure 4A:
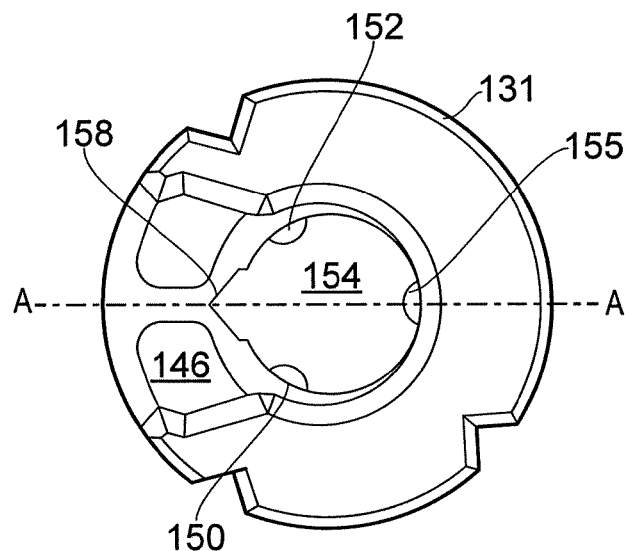
Figure 4B:
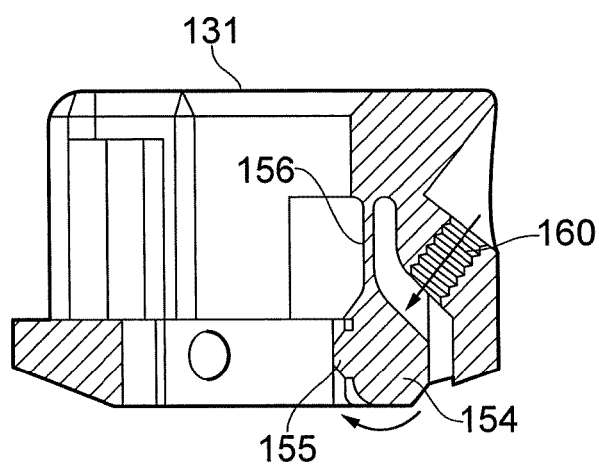
Figure 5:
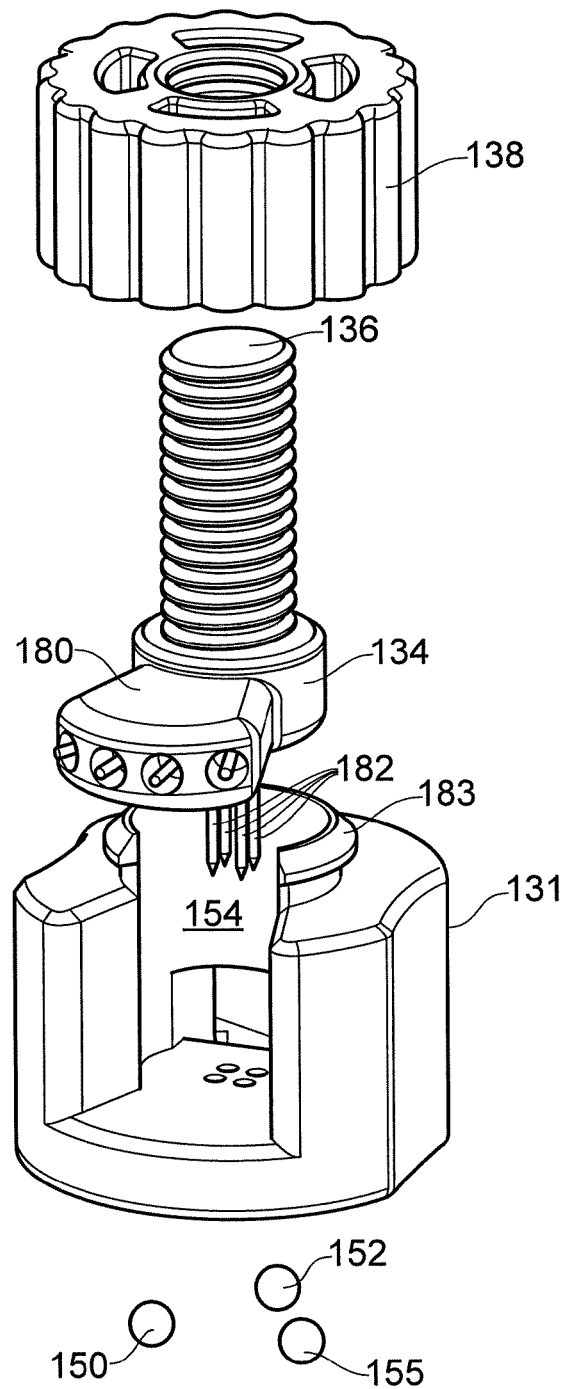
Figure 6A:
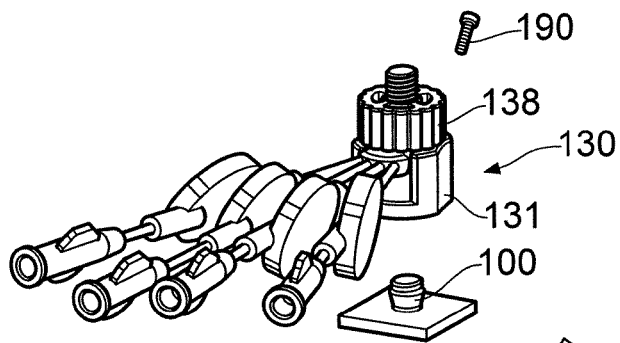
Figure 6B:
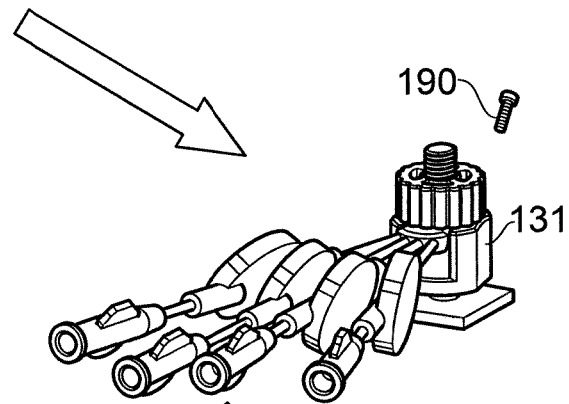
Figure 6C:
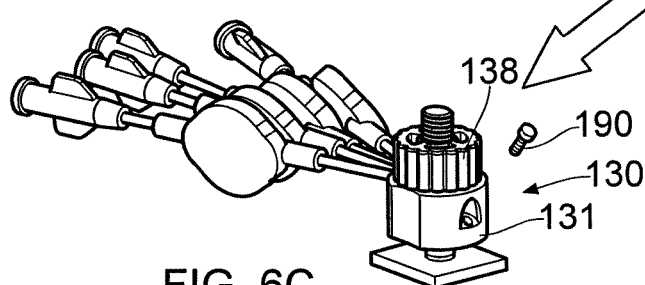
Figure 6D:
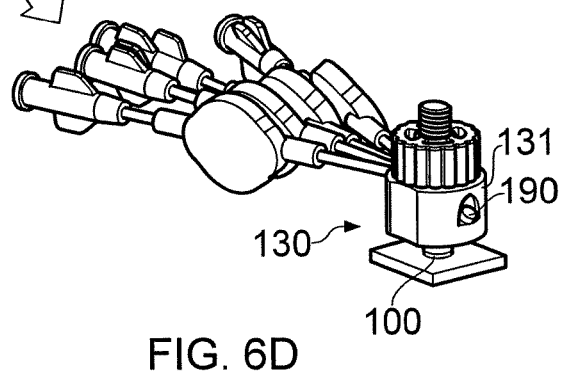
Figure 7A:
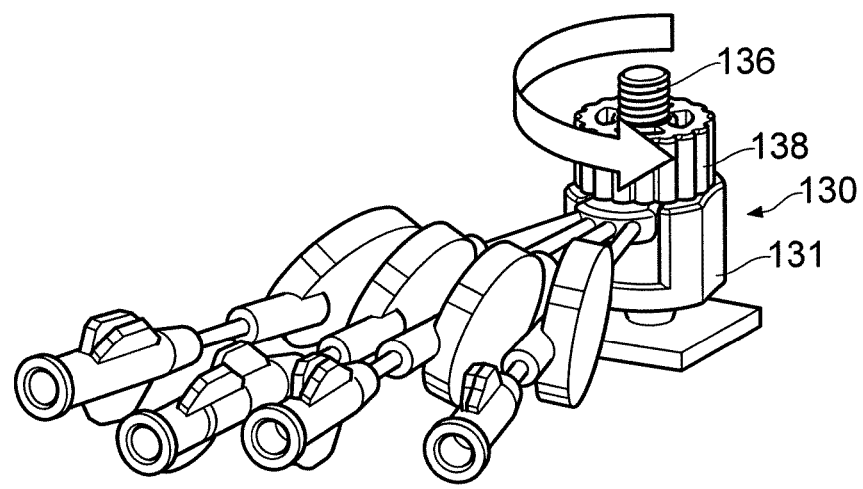
Figure 7B:
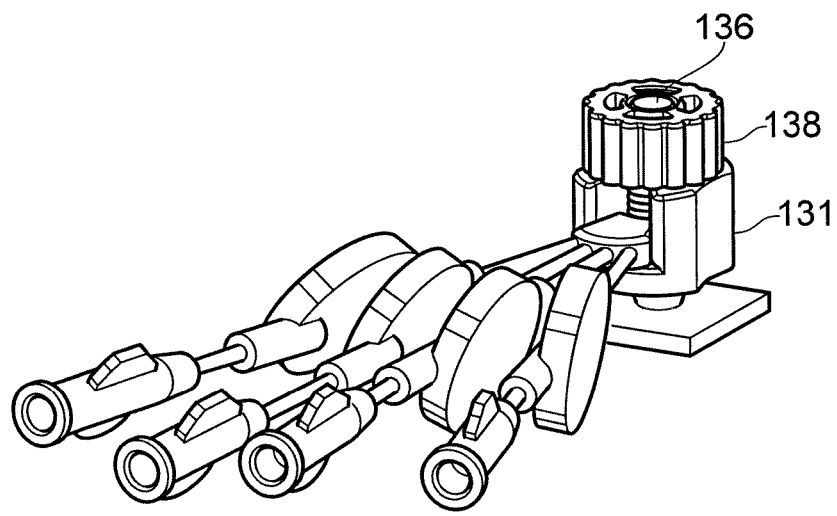
Figures 8A, 8B:
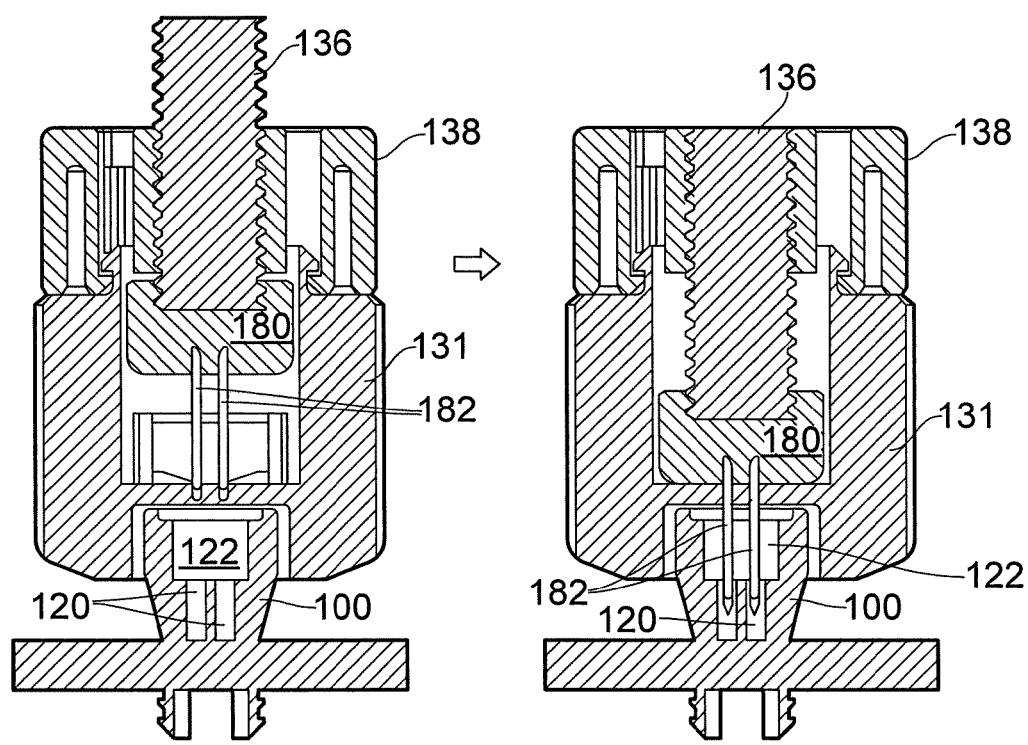
Figure 9:
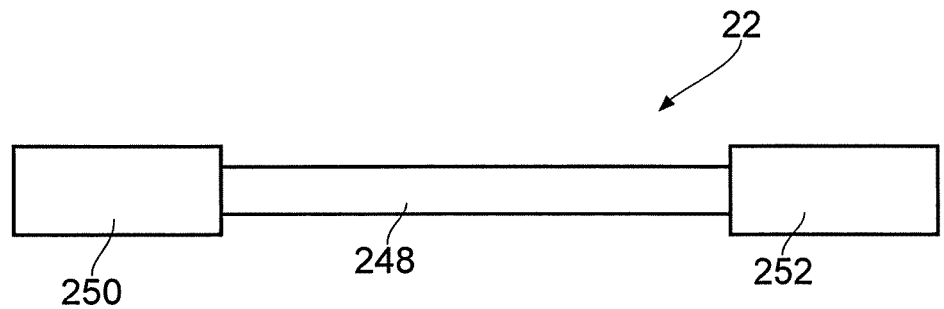
Figures 10A, 10B:
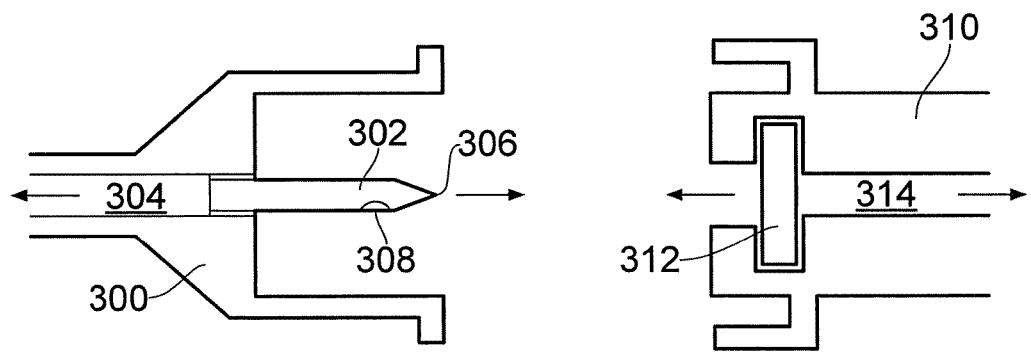
Figure 11:
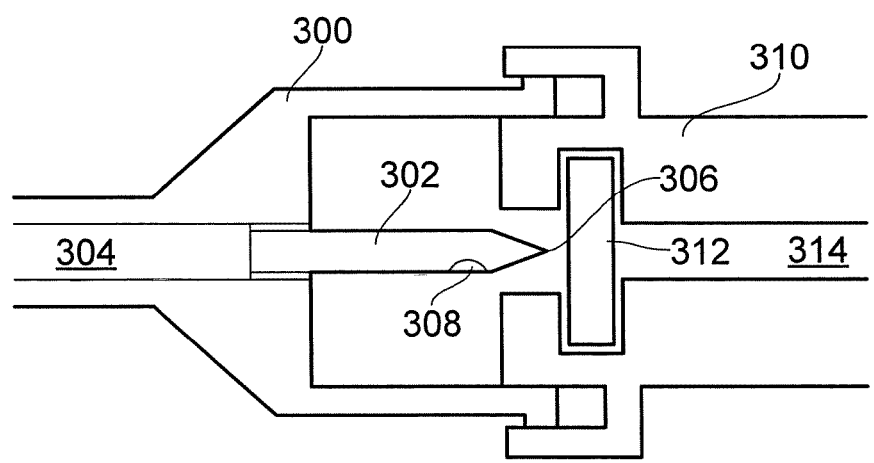
Figure 12:
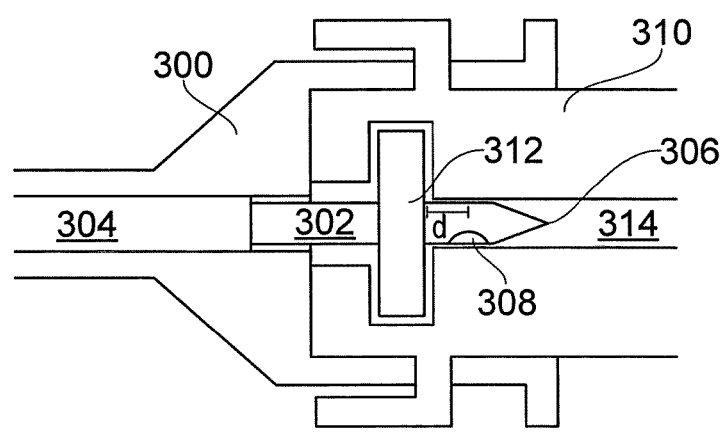

The invention will now be described, by way of example only, with reference to the accompanying drawings in which;

FIG. 1 shows a drug delivery system of the present invention,

FIGS. 2*a* and 2*b* show in more detail the implanted catheters and guide tubes of FIG. 1, FIGS. 3*a*, 3*b* and 3*c* show the percutaneous port and the connector device respectively of the percutaneous access apparatus shown in FIG. 1, FIGS. 4a and 4b show in more detail the guide member of the connector device of FIG. 3b, FIG. 5 shows in more detail the needle holding member of the connector device of FIG. 3b, FIGS. 6a to 6d show how the connector device is secured to the percutaneous port, FIGS. 7a and 7b illustrate how turning the knurled ring of the connector device forces the needles of the needle holding member through the septa of the percutaneous port, FIGS. 8a and 8b are cross-sectional views of the illustrations of FIGS. 7a and 7b respectively, FIG. 9 illustrate a drug storage tube, FIGS. 10a and 10b show modified Luer connectors, FIG. 11 shows the Luer connectors of FIGS. 10a and 10b aligned relative to one another, FIG. 12 shows the Luer connectors of FIGS. 10a and 10b connected to one another, and FIG. 13 shows an alternative embodiment of the connector device.

Referring to FIG. 1, an overview of the apparatus for delivering fluid to the brain is illustrated when implanted in a subject.

The apparatus comprises four fine catheters 2, each catheter being inserted into the brain via a previously implanted guide tube 4 (although it should be noted that only two of these are shown in FIG. 1). Suitable stereotactic insertion apparatus and methods have been described elsewhere previously, for example see U.S. Pat. No. 7,329,262 for details of a stereoguide based catheter insertion procedure. Supply tubing 6 runs from each catheter 2 to a hub 8. The hub 8 is connected by a length of multi-lumen tubing 10 to percutaneous access apparatus 12. The catheters 2, guide tubes 4, supply tubing 6, hub 8 and multi-lumen tubing 10 are all subcutaneously implantable (i.e. buried beneath the skin of the patient).

The percutaneous access apparatus 12 comprises a percutaneous fluid access device that is anchored directly to the skull of the patient. The percutaneous fluid access device comprises an extracorporeal portion to which an associated connector device is releasably attached. The percutaneous access apparatus 12 thus enables a fluidic link to the implanted catheters 2 to be established when required. In particular, the arrangement provides a separate, isolated, fluidic pathway to each catheter 2. More details about the percutaneous access apparatus 12 are provided below.

Outside of the body, the connector device of the percutaneous access apparatus 12 is linked to four external supply tubes 14. Each supply tube 14 includes an in-line bacterial and/or air filter 16. A four channel syringe pump 18 (which may comprise four separate single channel syringe pumps) is also provided. An outlet tube 20 from each channel of the syringe pump 18 is linked to one of the external supply tubes 14 via a drug storage tube 22. As will be explained in more detail below, each drug storage tube 22 is preloaded with a desired volume of therapeutic agent allowing the syringe pump 18 to be loaded with an inert solution (e.g. saline or artificial CSF). Fluidic connections between the drug storage tube 22 and the outlet tubes 20 and supply tubes 14 are made using low dead volume Luer lock connectors 24 of the type described in more detail below.

In use, the catheters 2, guide tubes 4, supply tubing 6, hub 8 and multi-lumen tubing 10 are all subcutaneously implanted in the subject (i.e. the skin flap 23 showed in a raised position in FIG. 1 is folded down and sutured in place). The percutaneous fluid access device of the percutaneous access apparatus 12 is also secured in place (e.g. attached to the skull and left protruding through the scalp) thereby providing the required fluid connection as and when required. These components are preferably suitable for long term implantation within a subject. For example, they may be designed to remain implanted for months or years.

When delivery of therapeutic agent is required, the connector device is attached to the percutaneous fluid access device. The supply tubes 14 (pre-primed with inert fluid) are then connected to the syringe pump via drug storage tubes 22 that contain the required dosage of therapeutic agent that is to be delivered. Each channel of the syringe pump is arranged to expel inert fluid (saline, artificial CSF etc) thereby pushing the therapeutic agent through the apparatus and expelling it from the tips of each catheter 2. The rate of fluid flow can be precisely controlled using the syringe pump 18 and the amount of therapeutic agent can be precisely set by defining the volume of the drug storage tubes 22. It is possible for fluid delivery to be continuous or intermittent. Fluid may also be delivered through all, or just some, of the catheters in parallel and/or it may be delivered sequentially through a sub-set of one or more catheters in turn. The precise delivery protocol can be set by a clinician.

Turning to FIGS. 2a and 2b, the fine catheter 2 and guide tube 4 of the apparatus described with reference to FIG. 1 are illustrated in more detail.

The guide tube 4 comprises an elongate tube 62 having a head 64 at its proximal end. The head 64 has a screw thread formation 66 on its outer surface that allows it to be secured to a burr hole formed in the skull by a press-fit action. The catheter 2 comprises a length of fine tubing for insertion into the lumen of the guide tube. The distal end or tip of the fine tubing of the catheter 2 extends beyond the distal end of the elongate tube 62 when inserted therein and comprises a hole for dispensing fluid. A hub 56 is provided at the proximal end of the fine tubing of the catheter 2. Further details of such a guide tube and catheter combination are outlined in WO2003/077785.

Referring to FIGS. 3A, 3B and 3C, the percutaneous access apparatus 12 of FIG. 1 is illustrated. FIGS. 3A and 3B illustrate the percutaneous fluid access device 100 that is implanted in the subject and FIG. 3C shows the external connector device 130 that attaches to the percutaneous fluid access device 100 whenever fluid delivery is required.

Referring to FIGS. 3A and 3B, the percutaneous fluid access device 100 comprises a subcutaneous portion 102, a percutaneous portion 104 and an extracorporeal portion 106.

The subcutaneous portion 102 is substantially cylindrical with protruding ribs 108 that enable secure attachment of the device to a hole formed in the skull via an interference or press fit. The external surface of the subcutaneous portion 102 is also roughened to promote osseointegration after implantation. The ribs 108 have an inclined surface that is at an angle θ of between 15 and 35 degrees to the longitudinal axis; this helps retain the device securely in place after implantation.

The percutaneous portion 104 (which can also be termed a transcutaneous portion) is the part of the device that passes through the skin. The surface of the percutaneous portion 104 is also roughened to promote skin in-growth after implantation thereby reducing the risk of infection. The percutaneous portion 104 is conical (i.e. it increases in diameter from skin surface) with an angle from the vertical of between 5 and 40 degrees.

The extracorporeal portion 106 is the part of the device that protrudes above the outer surface of the dermis. The extracorporeal portion 106 thus has a smooth surface to prevent tissue in-growth; such a smooth surface also allows it to be easily cleaned thereby reducing the chance of bacterial retention.

The extracorporeal portion 106 has a substantially cylindrical outer surface with a conical recess 109 and two v-shaped grooves 110 spaced apart around its circumference. A macro-alignment feature 112 is also provided. The conical recess 109 and grooves 110 act as very precise (kinematic) location features for the associated connector device, whilst the macro-alignment feature 112 ensures the connector device is in the approximately correctly orientation prior to attachment. Further details of the connector device are provided below.

As shown in the cross-sectional views of FIG. 3B, the percutaneous fluid access device 100 comprises four ports 120. Each port 120 is in fluid communication with a lumen of the multi-lumen supply tube 6. The supply tube 6 exits the subcutaneous portion 102 from its side and, when implanted, runs a short distance in a channel formed in the bone. The four ports 120 are accessible from the extracorporeal portion via a septum 122. In particular, each port 120 comprises an elongate channel having an axis substantially parallel to the longitudinal axis of the device. A single septum 122 that is accessible from the extracorporeal portion seals the end of the channel of all four ports. During fluid delivery, hollow needles of the connector device pierce the septum, enter the channels and thereby provide the required fluid communication with each port. In the absence of an attached connector device, the septum seal provides a fluid seal for all ports that prevents leakage of fluid or ingress of unwanted material (e.g. bacteria etc). FIG. 3B also shows in dashed outline the location of the dermal layer 121 and underlying bone 123 when the device is implanted.

FIG. 3C shows the connector device 130 for attachment to the percutaneous fluid access device 100. The connector device 130 comprises a connector base 131 having an attachment mechanism for securing the connector device 130 to the percutaneous fluid access device 100 in a precisely define relative position. The connector device 130 also includes a needle holder 134 attached to the end of a shaft 136. The shaft 136 has an external thread that engages a corresponding internal thread of a knurled portion 138. The needle holder 134 is located within a guide channel inside the connector base 131 and rotation of the knurled portion 138 relative to the connector base 131 drives the needle holder 134 back and forth along the channel. After the connector base 131 has been attached to the percutaneous fluid access device 100 by the attachment mechanism 132, the knurled portion 138 can be rotated to drive the hollow needles held by the needle holder 134 through the septum of the percutaneous fluid access device 100 thereby establishing the required fluid communication. The supply tubes 16 connected to the needles of the needle holder 134 are also shown. More details of the various components of the percutaneous fluid access apparatus are provided below.

Referring to FIGS. 4a and 4b, the attachment mechanism of the connector base 131 mentioned with reference to FIG. 3c is illustrated.

FIG. 4A shows a top-down view of the connector base 131 of the connector device 130. As explained above, the connector base 131 is configured to be releaseably attachable to the percutaneous fluid access device 100. The connector base 131 has a generally cylindrical outermost surface with a fluted slot 146 formed along one side and internal lip 148 at the lower end. The inner walls of the connector base 131 are generally cylindrical and define a guide channel 154 along which an associated needle holder 134 (not shown) can slide. The connector base 131 also includes an attachment mechanism 132 that comprises two fixed balls 150 and 152. A floating ball member 154 comprising a third ball 155 is carried by a hinge 156 (not shown in FIG. 4A). A macro-alignment feature in the form of a v-shaped slot 158 is formed in the internal lip 148.

FIG. 4B is a sectional view of the connector base 131 along the line A-A shown in FIG. 4A. The hinge 156 carrying the floating ball member 154 is shown. An elongate aperture 160 having an internal screw thread is also provided adjacent the hinge 156 and ball member 154. The elongate aperture 160 is arranged so that the tip of a screw (not shown) inserted through the aperture will protrude from the aperture and engage the floating ball member 154. Tightening the screw thus deflects the floating ball member 154 (i.e. it pivots at the hinge 156) thereby moving the ball toward the centre of the connector base. This allows the connector base 131 to be locked onto the percutaneous fluid access device 100 when required. The floating ball member 154 springs back when the screw is removed, thereby allowing the connector base 131 to be removed from the percutaneous fluid access device 100.

Moreover, the relative positions of the connector base 131 and percutaneous fluid access device 100 are defined by the engagement of the three ball of the connector base (i.e. the two fixed balls 150 and 152 and the third ball 155) with the grooves 110 of the percutaneous fluid access device 100. This arrangement, which is typically called a kinematic connection or kinematic joint, provides a highly repeatable mechanical linkage in which the six points of contact between the balls and grooves constrain the six degrees of freedom of movement between the connector base 131 and percutaneous fluid access device 100. This precise alignment ensures the hollow needles of the needle holder 134 (not shown) are correctly positioned relative to the ports of the percutaneous fluid access device 100.

It should be noted that, instead of the hinge 156 and floating ball member 154 arrangement shown in FIGS. 4A and 4A, various alternative arrangements could be implemented. For example, the tip of the screw could comprise a ball that directly engages a feature (e.g. groove) of the percutaneous fluid access device. A cam and lever arrangement could also be used instead of a screw to bias the floating ball member into contact with the percutaneous fluid access device.

Referring to FIG. 5, there is provided an exploded view of the connector device 130. The connector base 131 is arranged to receive a needle holder 134. The needle holder 134 comprises a substantially flat, keyhole shaped, supporting member 180. Four hollow needles 182 project perpendicularly from the flat surface of the supporting member. The four hollows needles 182 are spaced apart in a configuration that matches the arrangement of the ports of the percutaneous fluid access device 100. The needle holder 134 is also shaped to fit within, and slide along, the guide channel 154 of the connector base 131 that is described above. The needle holder 134 also includes four internal channels that provide separate fluidic channels between the lumens of the four hollow needles 182 and the four supply tubes 14. The screw threaded shaft 136 attached to the needle holder 134 is held by the threaded inner surface of the knurled portion 138. A lip 183 protruding from the connector base 131 secured the knurled portion 138 to the base 131.

Referring to FIGS. 6a to 6d, the procedure for locking the connector device 130 to the percutaneous fluid access device 100 is illustrated.

FIG. 6a shows the connector device 130, a screw 190 and a percutaneous fluid access device 100. FIGS. 6b and 6c show how the connector base 131 of the connector device 130 can be located on the percutaneous fluid access device 100. FIG. 6d shows the screw 190 inserted into the elongate aperture 160 of the connector base 131 and tightened so that the three ball of the connector base (i.e. the two fixed balls 150 and 152 and the third ball 155 shown in FIGS. 4a and 4b) firmly engage the recess 109 and grooves 110 of the percutaneous fluid access device 100. The connector device 130 is thus locked to the percutaneous fluid access device 100 (although no fluid linkage has yet been established).

Referring to FIGS. 7A, 7B, 8A and 8B, the procedure for establishing a fluid connection is illustrated. FIGS. 7A and 8A show the configuration of the connector device 130 after it has been locked to the percutaneous fluid access device 100. The hollow needles 182 of the needle holder 134 are positioned above the septum 122 in alignment with the respective channels of the ports 120. The connector base 131 is held in one hand whilst the other hand rotates the knurled portion 138 of the connector device 130 in an anticlockwise direction thereby driving the shaft 136 and needle holder 134 along the guide channel inside the connector base 131. As shown in FIG. 7B and 8B this translational motion of the needle holder along the guide channel causes the four hollow needles 182 to pierce the septum 122 and enter the four ports 120. Holding the connector base 131 ensures no torque is applied to the device-bone connection. In this manner, the four separate fluid pathways through the percutaneous access apparatus 12 are established.

Once the required fluid delivery has occurred, the knurled portion 138 can be rotated in a clockwise direction to withdraw the four hollow needles 182 back through the septum 122. The connector device 130 can then be unlocked from the percutaneous fluid access device 100 by removing the screw 190.

If required, the various components of the fluid delivery system can be MRI compatible.

Referring to FIG. 9, a drug storage tube 22 of the type described above is illustrated. The function of each drug storage tube 22 is to store the required volume of therapeutic agent that is to be dispensed through the associated catheter.

The drug storage tube 22 comprises a length of single lumen tubing 248 having a first end that terminates at a first fluid connector portion 250 and second end that terminates at a second fluid connector portion 252. The first and second fluid connector portions 250 and 252 are self-sealing connector portions that can mate with a complementary connector portion to establish a fluid link. For example, the first and second fluid connector portions 250 and 252 may be provided by a modified male Luer lock based connector portion of the type described in more detail below with reference to FIG. 10B.

The volume of the drug storage tube 22, including the dead volume of the first and second connector portions, is pre-selected to match the desired volume of fluid that is to be dispensed. In particular, the length of the single lumen tubing is pre-selected so that the internal volume of the drug storage tube 22 (including the dead volume of the connector portions) equals a desired value. In one example, the drug storage tube 22 may be pre-loaded with the desired volume (e.g. 300 μl ±6 μl) of GDNF. Once connected to an apparatus as shown in FIG. 1, the therapeutic agent can be pushed through the drug storage tube 22 by the flow of inert liquid from the pump and delivered to the patient.

A kit of drug storage tubes may also be provided. Each drug storage tube may comprise a certain, different, pre-defined volume. The required drug storage tube may then be selected and loaded with the appropriate drug as required. The procedure of loading the drug storage tube may be performed, for example, by a pharmacist.

FIGS. 10A and 10B illustrate a pair of mating Luer lock connectors that have been modified so as to have a low dead volume. Such connectors are suitable for applications, such as dispensing fluid to the brain, where low dead volumes are required due to the relatively low volumes of fluid being delivered. Preferably, the fluid path through the pair of connectors has a small and/or substantially invariant cross-sectional area. For example, the diameter of the fluid path may be about 0.7 mm. FIG. 10A shows a female Luer connector 300 in which a hollow needle 302 has been attached to the end of the lumen 304. The hollow needle 302 has a sharp tip 306 and a fluid aperture 308.

FIG. 10B shows a male Luer connector 310 in which a septum 312 has been inserted near the end of the lumen 314. The inclusion of the septum 312 in the male Luer connector 310 provides a fluid seal in the absence of an associated female Luer and also minimises the dead volume of the male Luer connector 310.

FIG. 11 shows the female Luer connector 300 aligned with the male Luer connector 310 prior to connection. FIG. 12 shows the male and female Luer connectors after engagement by a twisting action. In particular, the septum 312 of the male Luer connector 310 is pierced by the needle 302 of the female Luer connector 300 thereby providing a fluidic connection. The aperture 308 of the needle 302 is located a small distance d from the septum.

FIG. 13 shows an alternative connector device 430 suitable for attachment to the percutaneous fluid access device 100. The connector device 430 includes a connector base 432 that can be locked to the percutaneous fluid access device 100 in the manner described with reference to FIGS. 4a and 4b above. An additional guide device 434 is provided that can be secured to the connector base 432 after the base has been locked to the percutaneous fluid access device 100. A needle holder 436 is attached to the end of an elongate shaft 438 by a screw thread. The needle holder 436 and elongate shaft 438 may then be inserted into the channel of the additional guide device 434 and pushed along the channel until the hollow needles 440 of the needle holder engage and pierce the septum of the attached percutaneous fluid access device 100. The additional guide device thus ensures the needles are guided into contact with the septum from the required direction thereby reducing the risk of the septum being damaged. The additional guide device 434 may be detached from the connector base 432 after the fluidic connection has been established.

It should be remembered that the above are merely examples of the various aspects of the present invention.

The invention claimed is:

1. A percutaneous access apparatus comprising:
   a percutaneous fluid access device comprising an extracorporeal portion, one or more ports accessible from the extracorporeal portion and a septum for sealing each port, and
   a connector device comprising a body and a needle holder holding one or more hollow needles, the needle holder being moveable within the body,
   wherein the apparatus includes an attachment mechanism for attaching the connector device to the extracorporeal portion, and an actuation mechanism that, after the connector device has been attached to the extracorporeal portion, can be used to move the needle holder within the body to thereby drive the one or more hollow needles through the septum to establish fluid communication between the one or more hollow needles and the one or more ports.

2. An apparatus according to claim 1, wherein the attachment mechanism comprises a first set of features on the extracorporeal portion and a second set of features on the connector device, wherein the first and second sets of features provide, when engaged, accurate alignment of the connector device with the extracorporeal portion.

3. An apparatus according to claim 1, wherein the attachment mechanism provides a kinematic, or pseudo-kinematic, connection between the extracorporeal portion and the connector device.

4. An apparatus according to claim 1, wherein the one or more hollow needles comprise a plurality of hollow needles and the one or more ports comprise a plurality of ports, wherein the attachment mechanism allows repeatable alignment of each hollow needle with a predetermined respective one of the ports.

5. An apparatus according to claim 1, wherein the attachment mechanism comprises a locking device for releasably locking the connector device to the extracorporeal portion, the connector device comprising the locking device.

6. An apparatus according to claim 5, wherein the locking device comprises a screw and a hinged engagement member, wherein tightening the screw forces the hinged engagement member into contact with the extracorporeal portion thereby locking the connector device to the extracorporeal portion.

7. An apparatus according to claim 1, wherein the needle holder is retained within an axial alignment channel formed within the connector device.

8. An apparatus according to claim 7, wherein the actuation mechanism can be actuated to drive the needle holder back and forth along the alignment channel.

9. An apparatus according to claim 8, wherein the actuation mechanism comprises a threaded shaft and a rotatable knurled hub having a threaded channel, the needle holder being attached to a distal end of the threaded shaft and the threaded shaft being retained in the threaded channel of the rotatable knurled hub, wherein rotation of the knurled hub translates the needle holder back and forth along the alignment channel.

10. An apparatus according to claim 1, wherein the percutaneous fluid access device comprises a subcutaneous base portion through which the one or more ports extend, wherein the subcutaneous base portion comprises one or more port outlets for connection to one or more implanted catheters.

11. An apparatus according to claim 1, wherein the percutaneous fluid access device comprises a subcutaneous base portion, the subcutaneous base portion being at least partially insertable into a complementary recess formed in a bone, the subcutaneous base portion comprising one or more features for gripping an internal surface of the complementary recess thereby directly anchoring the subcutaneous base portion to the bone.

12. An apparatus according to claim 1, wherein the percutaneous fluid access device comprises printed titanium.

13. An apparatus according to claim 1, wherein the one or more ports comprise a plurality of ports and the septum is a single septum provided to cover each of the plurality of ports, wherein the single septum can be accessed and removed via the extracorporeal portion of the percutaneous fluid access device.

14. A connector device for attachment to a percutaneous fluid access device having one or more ports and a septum for sealing each port, the connector device comprising:
 a body and a needle holder holding one or more hollow needles, the needle holder comprising a threaded shaft and being moveable within the body,
 an attachment mechanism for attaching the body of the connector device to an extracorporeal portion of the associated percutaneous fluid access device, and
 an actuation mechanism comprising an internally threaded portion that engages the threaded shaft and drives the one or more hollow needles towards the septum of the associated percutaneous fluid access device when the threaded portion is rotated to thereby provide fluid communication between the one or more hollow needles and the one or more ports of the associated percutaneous fluid access device.

15. A connector device according to claim 14, wherein the needle holder surrounds at least a portion of an outer surface of at least one of the one or more hollow needles.

* * * * *